US00PP29463P2

(12) United States Plant Patent
O'Connell

(10) Patent No.: US PP29,463 P2
(45) Date of Patent: Jul. 3, 2018

(54) ***SEDUM X TACITUS* PLANT 'SPRING GLOW'**

(50) Latin Name: ***Sedum* x *Tacitus hybrida***
Varietal Denomination: Spring Glow

(71) Applicant: Altman Specialty Plants, Inc, Vista, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 15/731,162

(22) Filed: Apr. 26, 2017

(51) Int. Cl.
*A01H 5/00* (2018.01)
*A01H 5/02* (2018.01)

(52) U.S. Cl.
USPC ..... Plt./479
CPC ..... *A01H 5/02* (2013.01)

(58) Field of Classification Search
USPC ..... Plt./479
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Sedum*×*Tacitus* cultivar named 'Spring Glow' is disclosed, characterized by having lime green foliage flushed red in Winter months. Plants are densely mounding and offset freely. Plants are compact and produce offsets prolifically, useful for many pot sizes. Flowers are light salmon pink and occur on somewhat broad, open inflorescences. The new variety is an intergeneric hybrid *Sedum*×*Tacitus*, part of the Crassulaceae family. Plants are useful for a variety of ornamental purposes, including outdoor containers and landscape.

3 Drawing Sheets

Latin name of the genus and species: *Sedum* x *Tacitus hybrida.*

Variety denomination: 'SPRING GLOW'.

BACKGROUND OF THE INVENTION

The new *Sedum* x *Tacitus* cultivar is the product of a planned breeding program. The new variety originated from a cross pollination of the proprietary, unpatented, seed parent, *Sedum hybrida* referred to as 'Lime' with the pollen parent, an unpatented, proprietary variety of *Tacitus bellum* referred to as 'Dark Pink'. The crossing was made during April of 2012 at a commercial greenhouse in Vista, Calif.

'Spring Glow' was discovered by the inventor, Renee O'Connell, in February 2013, in Vista, Calif. at a commercial greenhouse in Vista, Calif.

Asexual reproduction of the new cultivar 'Spring Glow' was first performed in Vista, Calif., at a commercial greenhouse by vegetative cuttings, produced from side-shoots in September 2013. 'Spring Glow' has since produced multiple generations and has shown that the unique features of this cultivar are stable and reproduced true to type.

SUMMARY OF THE INVENTION

The cultivar 'SPRING GLOW' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPRING GLOW' These characteristics in combination distinguish 'SPRING GLOW' as a new and distinct *Sedum*x *Tacitus* cultivar:

1. As an intergeneric cultivar, the new variety exhibits characteristics of both *Sedum* and *Tacitus.*
2. Unique lime green foliage with marginal and apical red blush, most pronounced during Winter.
3. Broad, open inflorescence of distinctively large flowers.
4. Prolifically produces offsets, forming an attractive mounding cluster.

PARENTAL COMPARISON

Plants of the new cultivar 'SPRING GLOW' are similar to plants of the seed parent, in most horticultural characteristics, however, plants of the new cultivar 'SPRING GLOW' differ in the following;

1. 'Spring Glow' exhibits attractive reddish blushing of leaf during cooler weather, a characteristic not exhibited by the *Sedum* hybrid known as 'Lime'
2. 'Spring Glow' produces larger flowers, than the seed parent.
3. The parent *Sedum* hybrid known as 'Lime' grows with a somewhat open, lax morphology, while the new cultivar 'Spring Glow' exhibits a compact rosette morphology.
4. The parent *Sedum* hybrid known as 'Lime' eventually produces a branched plant, somewhat pendant, whereas 'Spring Glow' exhibits a compact mounding structure.
5. Flowers of the new variety are salmon pink, flowers of the seed parent are white.

Plants of the new cultivar 'SPRING GLOW' are similar to plants of the pollen parent, in most horticultural characteristics, however, plants of the new cultivar 'SPRING GLOW' differ in the following;

1. *Tacitus* 'Dark Pink' produces flattened rosettes of dark green leaves, whereas 'Spring Glow' forms rounded rosettes of lime green leaves.
2. 'Spring Glow' produces salmon pink flowers, whereas *Tacitus* 'Dark Pink' produces darker rose colored flowers.
3. 'Spring Glow' produces lime green leaves which blush reddish in cooler weather or drought, whereas the darker green leaves of the *Tacitus* 'Dark Pink' retain their same color despite drought or cooler weather.

COMMERCIAL COMPARISON

Plants of the new cultivar 'SPRING GLOW' are comparable to the known, unpatented, unnamed plant of *Tacitus bellus*. Plants are similar in most horticultural characteristics; however, the new variety 'SPRING GLOW' differs in the following:

1. 'Spring Glow' forms mounded clusters to 6" in height and 8" or more in diameter, whereas the unnamed plant of *Tacitus bellus* has a very low morphology, and clusters will not exceed 2" in height, and it is unlikely that the unnamed plant of *Tacitus bellus* can grow to 8" in diameter.
2. 'Spring Glow' produces clusters of lime green rosettes, blushed red in cooler weather, whereas the unnamed plant of *Tacitus* produces rosettes of gray green leaves.
3. 'Spring Glow' displays broad sprays of salmon pink flowers, whereas the unnamed plant of *Tacitus bellus* produces carmine flowers in an erect cyme.

Plants of the new cultivar 'SPRING GLOW' can also be comparable to the known, unpatented, plant of *Sedum adolphi*. Plants are similar in most horticultural characteristics; however, the new variety 'SPRING GLOW' differs in the following:

1. The unnamed plant of *Sedum adolphi* produces lax, pendant stems in time, whereas 'Spring Glow' forms mounded clusters:
2. 'Spring Glow' produces salmon pink flowers whereas the unnamed plant of *Sedum adolphi* produces white flowers.
3. 'Spring Glow' produces lime green leaves, whereas the unnamed plant of *Sedum adolphi* produces yellow or yellow-orange leaves.
4. 'Spring Glow', during cooler weather or drought blushes red on the apical tips and margins of the leaves, whereas the unnamed plant of *Sedum adolphi* does not.

BRIEF DESCRIPTION OF THE PHOTOGRAPHS

The accompanying photographs in FIG. 1 and FIG. 2 illustrate in full color typical plants of 'CALYPSO' grown in a commercial greenhouse in Vista, Calif. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Sedum* ×*Tacitus* plant. The following photographs depict plants grown under natural light conditions of 3000-3500 foot-candles. Temperatures ranged from 3° C. to 39° C. night and day. No artificial light, photoperiodic treatments or chemical treatments were given to the plants.

DETAILED BOTANICAL DESCRIPTION

Figure 1:
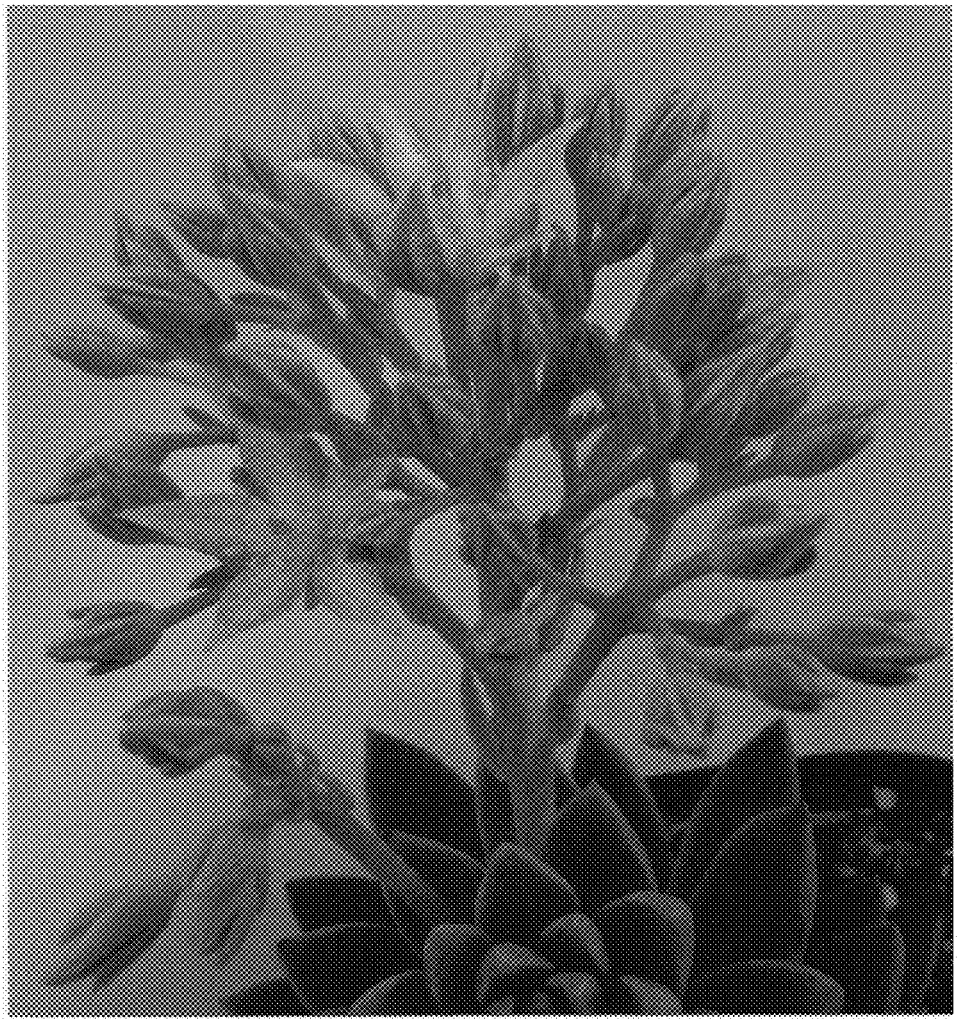
FIG. 1 illustrates in full color a close up of individual flowers and inflorescence of the new variety.
Figure 2:
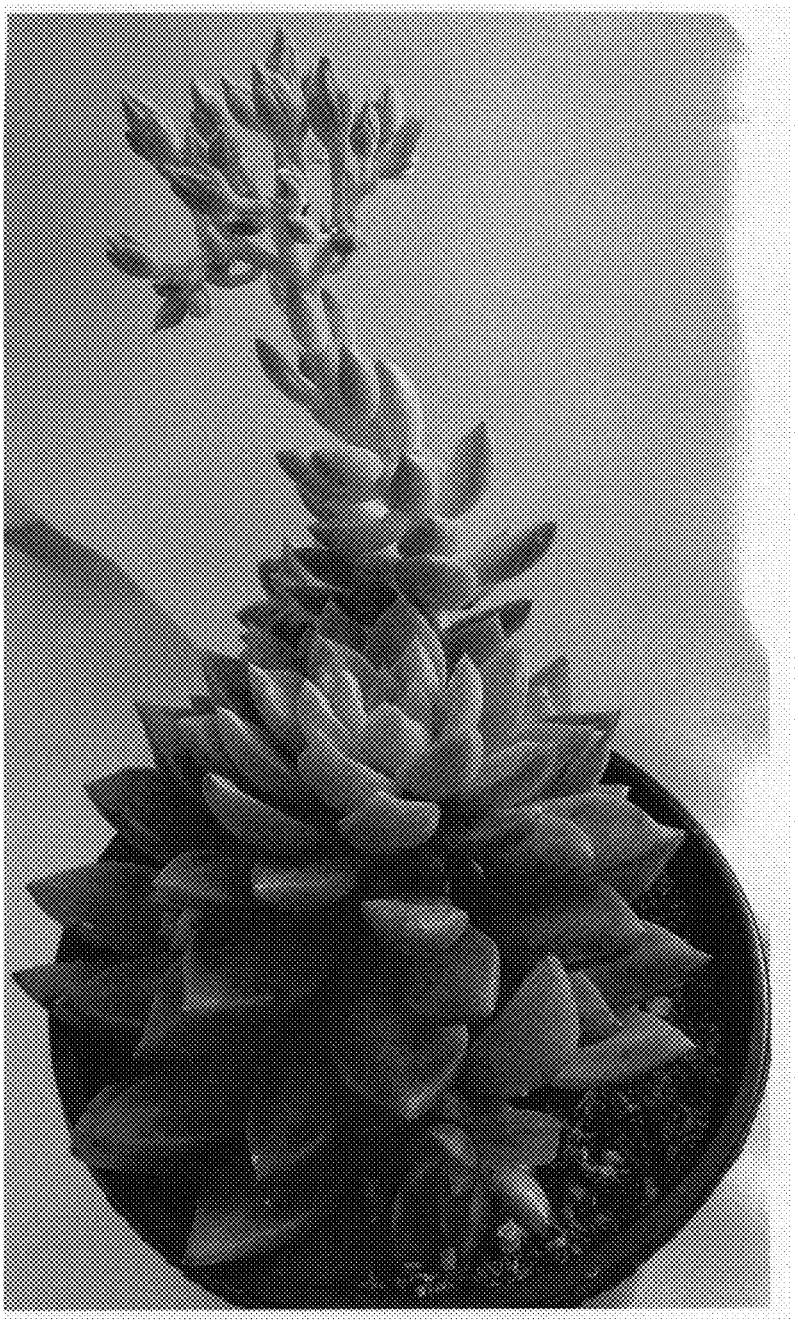
FIG. 2 illustrates in full color the side view of a typical plant of *Sedum* x *Tacitus* 'Spring Glow' during the Winter months.
Figure 3:
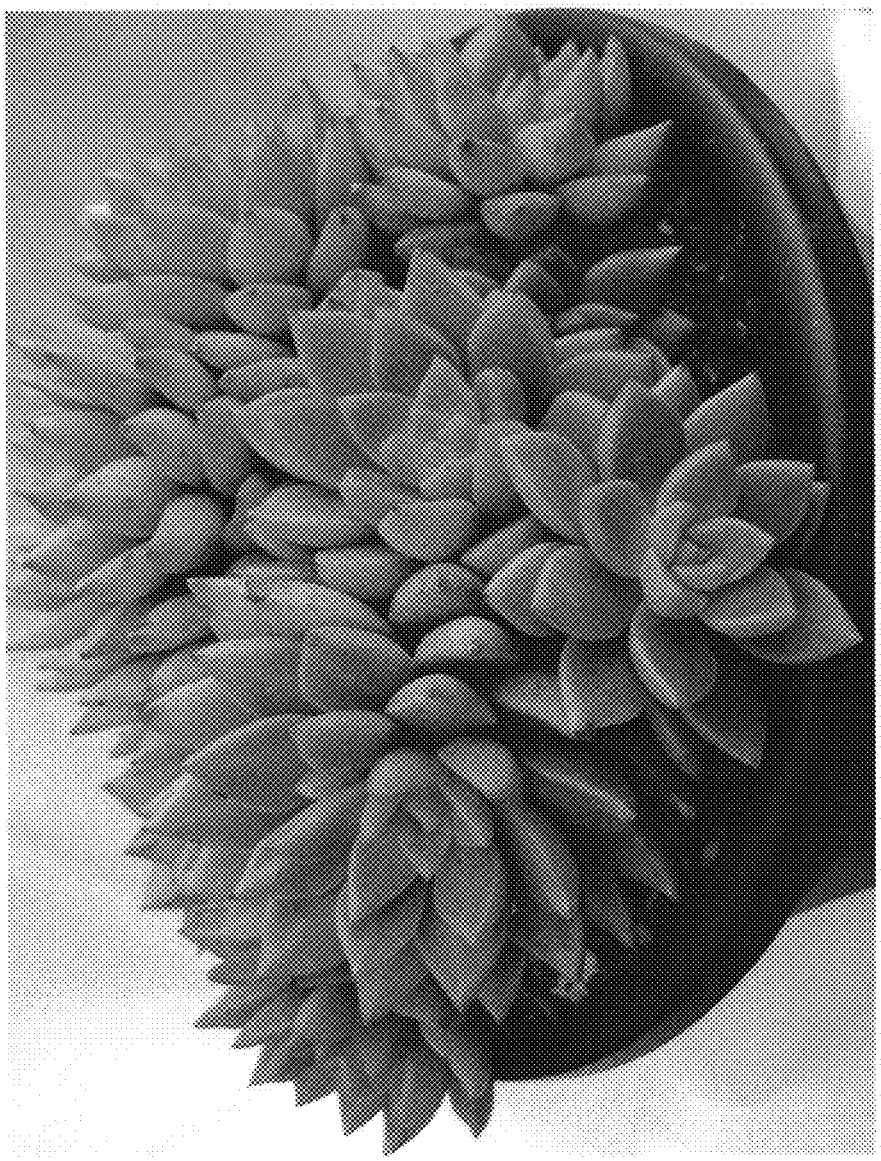
FIG. 3 illustrates in full color a non-flowering plant, just beginning to show reddish aspices.

In the following description, color references are made to The Royal Horticultural Society Colour Chart, 2007 except where general terms of ordinary dictionary significance are used. The following observations and measurements describe 'Spring Glow' plants in a commercial greenhouse in Vista, Calif. Temperatures ranged from approximately 10° C. to 38° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Sedum* ×*Tacitus hybrida* 'SPRING GLOW'.

PROPAGATION

Type of propagation typically used: Terminal vegetative divisions, offsets.

Time to initiate roots: About 14 days at approximately 22° C.

Root description: Fibrous, brown, not accurately measured with a color chart.

PLANT

Age of plant described: Approximately 4 months from a well rooted plantlet.

Container size of the plant described: 6 inch.

Growth habit: Densely rosulate, mounding, pup-forming.

Height: Approximately 7.0 cm to top of highest leaf Approximately 17 cm to top of highest inflorescence.

Plant spread: 11 cm.

Growth rate: Moderately fast.

Branching characteristics: Moderately freely offsetting. Approximately 3 offsets on a plant of this size and age.

FOLIAGE

Leaf:

*Arrangement*.—Rosulate.

*Average length*.—Approximately 4.0 cm.

*Average width*.—Approximately 1.5 cm.

*Width at base*.—0.9 cm.

*Average depth*.—Approximately 8 mm.

*Shape of blade*.—Spatulate, with overall apical shape somewhat angular and sloping.

*Apex*.—Mucronate.

*Base*.—Cuneate.

*Margin*.—Rounded.

*Texture of top surface*.—Glabrous, slightly glaucous.

*Texture of bottom surface*.—Glabrous, slightly glaucous.

*Quantity of leaves per rosette*.—Approximate range of 60 to 80.

Color:

*Young foliage upper side*.—Large basal section near White N155B. Midsection Green 138B, turning 138A towards apex. Apical margin Greyed-Purple 185B.

*Young foliage, under side*.—Large basal section near White N155B. Midsection Green 138C, turning 138B towards apex. Apical margin Greyed-Purple 185B.

*Mature foliage, upper side*.—Basal section near White N155B, turning Green 138D further up blade. Midsection Green 138B, turning 138A towards apex. Apical margin Greyed-Purple 183B. Upper ⅓ of blade flushed 183D.

*Mature foliage, under side*.—Basal section near White N155B, turning Green 138D further up blade. Midsection Green 138B, turning 138A towards apex. Apical margin Greyed-Purple 183B.

Venation: There is no visual appearance of venation.

FLOWER

Natural flowering season: Spring, Summer, irregularly.

Inflorescence type: Cyme, somewhat broad and open.

Inflorescence size (excluding peduncle):

*Height*.—Approximately 5 cm.

*Width*.—Approximately 8 cm.

*Quantity of inflorescence per plant:* 1-3 depending upon maturity.

Quantity of flowers per inflorescence: Average range 15 to 20.

Individual flowers:

*Length*.—Approximately 1.5 cm.

*Diameter*.—Approximately 2.3 cm.

Petals:

*Arrangement*.—Rotate.

*Quantity*.—4, 5 or 8.

*Size*.—Length: Approximately 0.8 cm. Width: Approximately 0.3 cm.

*Margin*.—Entire.

*Shape*.—Narrow deltate.

*Apex*.—Acute.

*Base*.—Fused, approximately 10% of length.

*Texture*.—Glabrous all surfaces. Petal Color: When opening: Petal color, outer surface: Near RHS Red 47B, streaked Red 48D. Petal color, interior: Not visible until flower matures. Petal Color, Fully opened: Outer surface: Near RHS Red 54A streaked Red 56D. Inner surface: Near RHS Red 49D, heavily flushed 53C. Apex 53A. Color Changes when Aging: Inner and outer surfaces fade, flowers colored mainly 49D and moderately flushed 53C. Bud: (near opening): Shape: Conical. Length: Approximately 1.2 cm. Diameter: Approximately 0.7 cm. Color: Near RHS Red 47B, streaked Red 48D. Sepals: Length of sepal: Approximately 0.6 cm long. Width of sepal: Approximately 0.2 cm at widest point. Color outer surface: Near RHS Green 138D, apical flush 183A. Color inner surface: Near RHS Green 138D, apical flush 183A.

*Peduncle*.—Length: Average range 4 to 9 cm. Width: Approximately 0.6 cm. Strength: Moderately strong. Texture: Glabrous. Color: Near RHS Greyed-Orange N170D.

*Pedicels*.—Length: Approximately 0.4 to 0.6 cm. Width: Approximately 0.2 cm. Aspect: Straight. Strength: Moderately strong. Color: Between Red 56A and Greyed-Red 179D.

*Fragrance*.—None detected.

REPRODUCTIVE ORGANS

Stamens: (Androecium).

*Number*.—Average 10.

*Filament length*.—Approximately 0.5 cm.

*Filament color*.—Near RHS White N155C.

*Anther length*.—0.1 cm.

*Anther color*.—Near RHS Yellow 10D.

*Anther shape*.—Oblong.

*Pollen color*.—Near RHS Yellow 11D.

*Pollen quantity*.—Scant.

Pistil: (Gynoecium).

*Number*.—Average 5.

*Length*.—Approximately 0.9 cm.

*Style color*.—Near Red 56D.

*Style length*.—Approximately 0.3 cm.

*Stigma*.—Shape: Linear. Color: Near Red 55D. Ovary Color: Near RHS Red 56D.

OTHER CHARACTERISTICS

Fruits and seeds: Typical to Genus. Minute, less than 1 mm dry seeds. Colored between black and brown, too small to accurately measure with color chart.

Temperature tolerance: Tolerates temperatures from approximately −2° C. to at least 35° C.

Disease/pest resistance: Neither resistance nor susceptibility to normal diseases and pests observed.

Drought tolerance: Tolerates at least 2 to 3 weeks of high temperatures without supplemental water, showing no serious damage to plant.

What is claimed is:

1. A new and distinct cultivar of *Sedum* x *Tacitus* plant named 'SPRING GLOW' as herein illustrated and described.

* * * * *